(12) United States Patent
Klein et al.

(10) Patent No.: US 7,513,861 B2
(45) Date of Patent: *Apr. 7, 2009

(54) REAL TIME VERIFICATION IN RADIATION TREATMENT

(75) Inventors: Michael Klein, Menlo Park, CA (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 113 days.

This patent is subject to a terminal disclaimer.

(21) Appl. No.: 11/394,640

(22) Filed: Mar. 31, 2006

(65) Prior Publication Data

US 2006/0241332 A1     Oct. 26, 2006

Related U.S. Application Data

(63) Continuation-in-part of application No. 10/464,140, filed on Jun. 18, 2003, now Pat. No. 7,322,929, and a continuation-in-part of application No. 11/324,772, filed on Dec. 31, 2005.

(51) Int. Cl.
*A61N 5/00* (2006.01)
(52) U.S. Cl. .......................................................... 600/3
(58) Field of Classification Search .................. 600/1–8
See application file for complete search history.

(56) References Cited

U.S. PATENT DOCUMENTS

| 6,251,059 | B1 * | 6/2001 | Apple et al. .................... 600/3 |
| 6,320,935 | B1 * | 11/2001 | Shinar et al. ................. 378/119 |
| 6,402,689 | B1 * | 6/2002 | Scarantino et al. .......... 600/300 |
| 7,322,929 | B2 | 1/2008 | Lovoi |
| 2005/0038468 | A1 | 2/2005 | Panetta et al. |
| 2005/0080340 | A1 | 4/2005 | Stewart et al. |
| 2005/0101824 | A1 | 5/2005 | Stubbs |
| 2006/0173233 | A1 | 8/2006 | Lovoi |

OTHER PUBLICATIONS

Gladstone, DJ and Chin, LM, "Automated data collection and analysis system for MOSFET radiation detectors", *Med. Phys.*, May 1991, vol. 18(3).
Scarantino, Ruslander et al., "An implantable radiation dosimeter for use in external beam radiation therapy", *Med. Phys.*, Sep. 2004, vol. 31(9), Sicel Technologies, Inc., Morrisvile, N.C.
Scarantino, Rini et al., "Initial clinical results of an in vivo dosimeter during external beam radiation therapy", *Med. Phys.*, Jun. 1, 2005, vol. 62(2), Sicel Technologies, Inc., Morrisville, N.C.
"Treating Cancer From The Inside Out", 2004, Varian Medical Systems, (Internet).

* cited by examiner

*Primary Examiner*—John P Lacyk
(74) *Attorney, Agent, or Firm*—Thomas M. Freiburger (57) ABSTRACT

A radiation therapy system and method, especially for brachytherapy, monitors and verifies dose delivered at a plurality of points at or near the region to be irradiated, integrating verification with radiation delivery. In one procedure, mapping is used to determine the shape and location of the region to be irradiated. A treatment plan is developed using the mapping information and a dose prescription. As radiation is delivered to the target region internally, preferably using an electronic radiation source, the dose received at plural points is monitored and continually fed to a central processor. As needed based on feedback, the system modifies the treatment plan and delivery of radiation accordingly, to arrive substantially at the prescribed dose at all locations in the region. In a modified procedure the treatment is done according to a prescription dose but without a treatment plan by multiple iterations of source pullback and feedback and analysis of dose received in the tissue. Source radiation levels and/or pattern and dwell are modified for each successive iteration and preferably for different dwell points in an iteration.

32 Claims, 8 Drawing Sheets

REAL TIME VERIFICATION IN RADIATION TREATMENT

This application is a continuation-in-part of application No. 10/464,140, filed Jun. 18, 2003, now U.S. Pat. No. 7,322, 929, which is fully incorporated herein by reference, and of application Ser. No. and is a CIP of 11/324,772, filed Dec. 31, 2005, also incorporated herein by reference.

BACKGROUND OF THE INVENTION

This invention concerns radiation therapy, usually as post operative or intra operative treatment to eradicate malignancies or other types of tissue. Specifically the invention concerns verification of dose delivered in a radiation treatment procedure, and can include real-time feedback to a controller, verification of treatment and modification of a treatment plan and of the radiation delivered in real time as needed based on monitored dose at one or more locations.

Radiation therapy, including with x-ray radiation, is used for several purposes on human beings, from treatment of minor skin cancers to post-operative treatment after resection of a tumor. In brachytherapy a radiation source is placed inside the patient for localization of the radiation treatment. In IMRT, intensity modulated radiation therapy, beams of radiation are directed from a series of external positions toward an internal target of the patient, and fingers shape the beam into beamlets for each treatment position, thus concentrating the desired radiation dose essentially at the target with the goal of delivering only harmless doses of radiation along the series of different paths. The IMRT radiation would better be characterized as "position modulated", or modulated as to a series of different angles of attack for the beams of radiation.

Although these and other types of radiation therapy have been improved in recent years and have become more specifically targeted and localized, achieving improvements in dose accuracy and better avoiding excessive dose to other tissue not to be irradiated, these radiation therapy techniques have not achieved localized verification of delivered dose or real-time correction of treatment and have not approached the accuracy, localization and safety of the current invention described below.

SUMMARY OF THE INVENTION

A radiation therapy system and method, especially for brachytherapy, monitors and verifies dose delivered at a plurality of points at or near the region to be irradiated and integrates verification with radiation delivery; including real-time modifications of the radiation during treatment.

Mapping can be used to determine the shape and location of the region to be irradiated, which can be a resection cavity or a body of tissue to be irradiated, such as a tumor not removed by resection. Specific techniques may be used for mapping the region, which can include the use of sensors and preliminary low-dose radiation as disclosed in the above-referenced 10/464,140 application. Alternatively CT scans (two-dimensional or three-dimensional) or ultrasound can be used for mapping the tissue location. In a preferred form of the system a treatment plan is developed using the mapping information and a dose prescription.

As radiation is delivered to the target region internally using an ionizing radiation source, preferably an electronic radiation source, the dose received at a plurality of points in or near the region is monitored, and this information is continually (or at increments) fed to a central processor. As needed during the delivery of radiation, the system modifies the treatment plan based on dose as determined, and modifies delivery of the radiation accordingly, to arrive substantially at a prescribed dose at all locations in the region.

In one preferred embodiment the monitoring and verifying steps are carried out using sensors located on the probe itself, which can be with or without a balloon. In another embodiment the sensors are positioned within a cavity at the region to be irradiated. In one particular embodiment, the region to be irradiated is tissue surrounding a cavity, and the monitoring and verifying sensors are carried on a balloon on the probe, the balloon being inflated in the cavity.

Another embodiment has the sensors positioned interstitially in the patient, near the region to be irradiated.

In still another form of the system, the sensors are located externally on a patient, such as on the outside surface of the patient's breast. Also, the sensors can be placed in a combination of the above locations, such as, for breast therapy, on the skin, at the chest wall and on the applicator balloon.

The monitoring and modification of the plan and delivery are carried out in real time, in the sense that changes are made during the procedure, in order to arrive at the final desired prescription dose at a number of different locations. The plan and the radiation delivery can be modified between fractions, or can even be modified within a single fraction; but in either event such modification prior to completion of the procedure is referred to herein as real-time modification.

In a principal aspect of the invention the radiation source is an electronic ionizing radiation source, which may be a miniature x-ray tube switchable on/off as well as voltage-variable and current-variable. This gives a wide range of choices for radiation depth penetration and cumulative dose, enabling a prescribed dose to be achieved much more precisely, especially with the real time monitoring and modification aspects of the invention.

Preferably a central processor or controller forms a part of the system, used to prepare the radiation treatment plan based on the determined shape and location of the region as well as on the prescribed dose profile, and also used to receive real-time monitoring information from the sensors and to modify the treatment plan in real time prior to full delivery of the prescribed dose. The controller can include or be linked to a manipulating device that pulls back the catheter or probe carrying the source and, in the case of directional radiation, that rotates the source and directs radiation in limited arcs as determined by the processor to implement the prescribed dose in substantially all areas of tissue while avoiding overdose to the skin and other sensitive tissue regions. Rather than (or in conjunction with) rotation the probe can have rotating shields or extendable/retractable finger-like shield segments, which can be manipulated by the controller.

In another implementation of the invention the treatment plan is eliminated, as is the need for precise pre-treatment mapping. Instead, with dosimeter sensors placed at adequate locations in, adjacent to or surrounding the target tissue, a pullback routine is initiated and several iterations are made. The pullback routine is not a treatment plan in the traditional sense, since irradiation level and dwell times are not calculated and implemented for a series of pullback dwell locations in an attempt to approximate the dose profile prescribed for the tissue. Instead, only a skeletal series of movements (or a continuous pullback) at a selected rate is used, and the processor calculates how to achieve the prescription dose at the multiple tissue locations, using a series of pullback iterations. In a first or preliminary or "pilot" pullback iteration, the system carries out a pullback routine at low levels of radiation, known to be insufficient, at the dwell times or pullback rate utilized, to reach the prescription dose in any region or to overdose any tissue, whether target tissue or adjacent tissue. For this purpose the electronic source can be powered to emit radiation at high penetration, i.e. high voltage, but at low current and short dwell times (or rapid pullback rate). Feedback from the sensors provides data to the processor, which carefully calculates the effect on the different regions of the radiation emitted from each dwell point (with interpolation and extrapolation as needed), thereby creating in effect a table relating to the effect of radiation from each dwell point, for use in completing the procedure. If needed for additional data in this regard, the electronic source can be directed to emit at a lower voltage, then at a high voltage at each dwell position.

Using these data, the processor calculates the radiation settings and dwell times (or pullback rate) needed for one or more successive iterations. This is done in a manner to protect skin, bones, vital organs and other critical tissues from receiving excessive dose. More than one further iteration is preferred, so the system can use conservative values in the second iteration so as to approach full prescription dose at all regions more conservatively.

As noted above, the controller or a manipulating device connected to the controller preferably rotates the catheter or probe (or manipulates a shielding device), carrying a directional radiation source, to enable discrimination among different rotational positions of tissue at each dwell location. Directionality at the source can be selectable, as by a sleeve-shaped shield that can be pulled back for omnidirectional radiation or pulled forward over the source, leaving a single window for directional radiation.

In this way, in a series of pullback iterations, the system approaches the prescription dose at all locations and completes the dose, where not already completed in some locations, in a final iteration. Prescribed dose at substantially all locations is thus achieved with very high accuracy and substantially without overdosing any tissue within the target region or elsewhere.

A radiology communication protocol known as Dicom RT can be used for communications between the processor and the sensors/system, and between the processor and the electronic radiation source or sources. A wireless protocol using ultra wide band (UWB), or another suitable protocol, can also be used. In one aspect of the invention the central processor or controller also is used to store patient information, including patient identity, history, schedule of prescribed radiation dose fractions, results of treatment, and other information.

It is thus among the objects of the invention to improve the accuracy, reliability and efficiency of brachytherapy radiation treatment through a closed-loop system that performs real-time monitoring or simply real-time monitoring and adjustments to radiation delivery and plan correction, as the treatment progresses. These and other objects, advantages and features of the invention will be apparent from the following description of preferred embodiments, considered along with the accompanying drawings.

DESCRIPTION OF PREFERRED EMBODIMENTS

The invention has several aspects. One of its primary aspects is real-time monitoring of radiation dose received at a particular site in a patient by measurement of the dose by sensors at the site or displaced from the site but with a reliable extrapolation (or interpolation) to calculate site dose received. Another aspect is the integration of subsystems in a radiation treatment program by continuous or nearly-continuous communication between subsystems, all under the control of a central controller or processor. This can include tagging other information to a file containing the real-time dose information and feedback, such as information regarding the patient, the patient's medical history, scheduled visits for radiation therapy, etc. Another important aspect is brachytherapy using the noted verification techniques, to provide the optimum localization and accuracy of the treatment.

Figure 1:
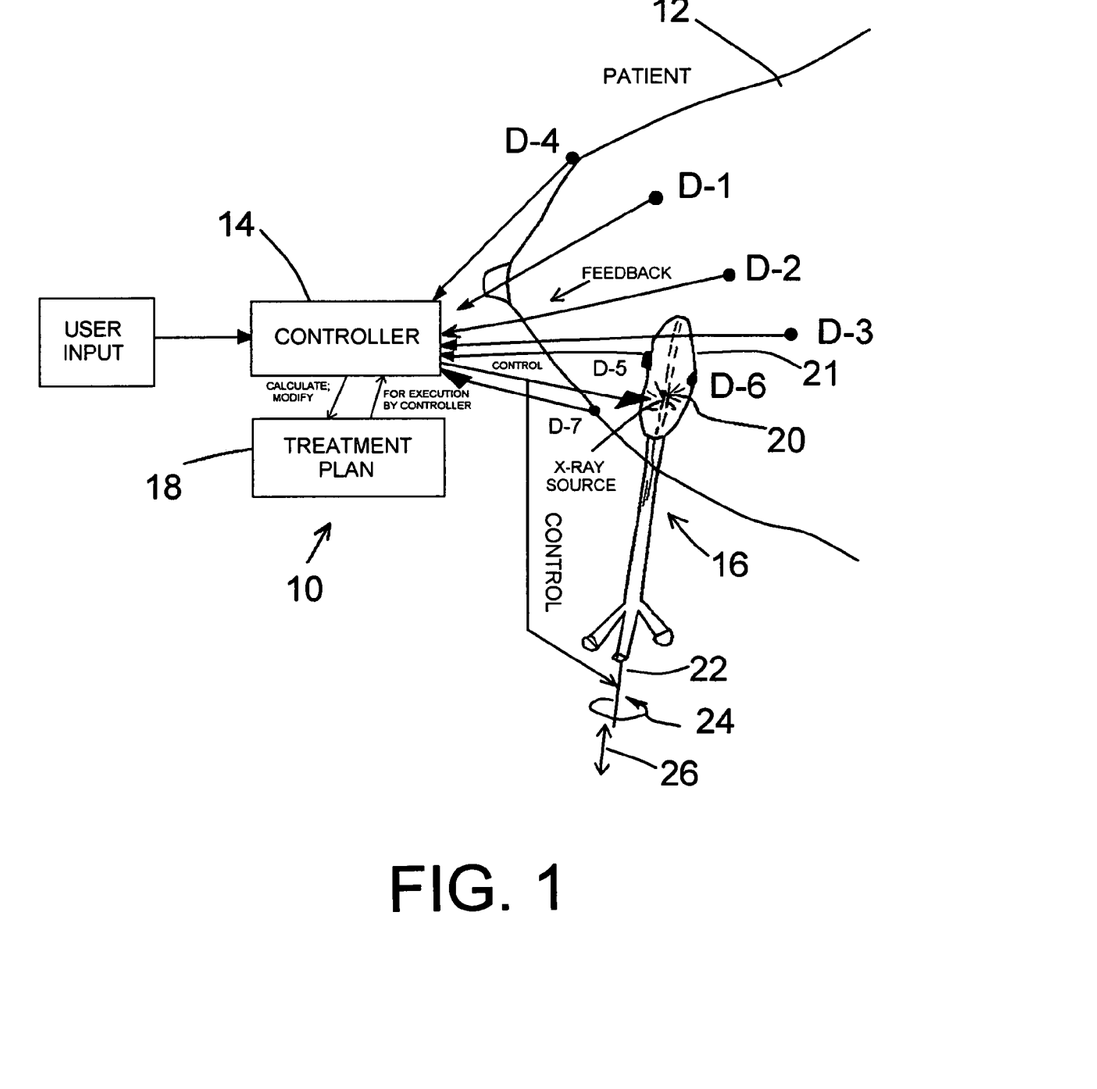
FIG. 1 is a somewhat schematic view, partially block diagram and showing control and information flow, and indicating a patient in breast radiation therapy utilizing the techniques, system and method of the invention.

FIG. 1 shows, very schematically, one implementation of the system of the invention. The drawing indicates the system 10 administering radiation therapy on a patient's breast 12. A controller or processor 14 is in communication with an applicator 16 and with a series of dosimeters shown as D-1 through D-7, some of which preferably are on the applicator 16, some of which may be located on the exterior skin surface of the breast and some of which may be positioned interstitially, as by insertion on the end of a needle. Wireless or wired connections can be employed to connect the dosimeters with the controller. The controller 14 is also shown in communication with a treatment plan 18, comprising software which is programmed by a user inputting to the controller/processor 14 and which program carries out a treatment plan using the applicator 16.

As schematically shown in FIG. 1, the applicator 16 has an electronic ionizing radiation source 20, preferably a miniature x-ray tube which is switchable on/off and controllable as to voltage and current, thus to control radiation penetration and dose delivered. The x-ray source 20 is retained on a catheter 22 which, in preferred embodiments, is also under machine control, via instructions from the controller/processor 14. The controller itself can include a manipulating device. In a preferred embodiment the catheter 22 can be rotated (as indicated at 24) and pulled back and pushed forward (as indicated at 26) by a machine. This can also be done by hand, by the radiologist, following the treatment plan, and the steps to be performed manually by the radiologist can be indicated on a screen, for example (not shown in FIG. 1).

The applicator 16, especially for irradiation in a resection cavity, can have a balloon 21, and several dosimeter sensors are advantageously located on the balloon to be adjacent to tissue (D-5 and D-6 are shown on the balloon).

As explained above, it is an important and central feature of the invention that real-time monitoring be used, by the dosimeters sensing radiation dose at one or more locations near the tissue to be irradiated. The system feeds back received dose information to the processor 14, which in turn adjusts the emission of radiation from the electronic x-ray source 20 during the procedure or between fractions, and in any event prior to completion of the radiation treatment, whether in one fraction or several. The feedback control of the invention allows for a high degree of accuracy in achieving the prescription dose to the target tissue, while also minimizing radiation exposure and consequent damage to other tissue structures such as the skin and the chest wall, as disclosed in copending application Ser. No. 10/464,140, incorporated herein by reference. With the controllability of the x-ray source 20 of the invention, and the control afforded by feedback from the dosimeters at various locations, including on the applicator or at adjacent tissue, and real-time modifications of treatment by the processor 14, dose can be measured and end point dose extrapolated based on current settings at a number of locations. This is true not only for dosimeter points but for nearly all tissue locations, and excessive radiation to the skin or to the chest wall, bones or other critical areas can be avoided through this control.

The invention can be used with an isotope source also, with the control aspects directed to dwell times and optionally shielding or partial shielding for radiation levels and directionality.

In one implementation of the invention a detailed treatment plan can be calculated and prepared from the dose profile prescribed by the physician for the target tissue, which may be a body of tissue surrounding a resection cavity, with the treatment plan including control of voltage and/or current to the source 20 as well as stepped pullback locations and dwell times. A previous mapping of the tissue can provide information needed for the treatment plan, that is, localization of the region to be irradiated. Moreover, the detailed treatment plan can further include use of directional radiation from the source 20, along with rotation of the catheter 22 and modification of the radiation hardness and dose delivered based not only on step location but also on rotational direction of radiation. The source 20 can be a permanently directional source and rotatable, or movable shielding can be included, such as an axially movable shield or shield segments as part of the catheter, to selectively shield the source at most of its circumference when pushed forward (distally), and which can be controlled from the proximal end of the catheter 22.

Figures 1A, 1B:
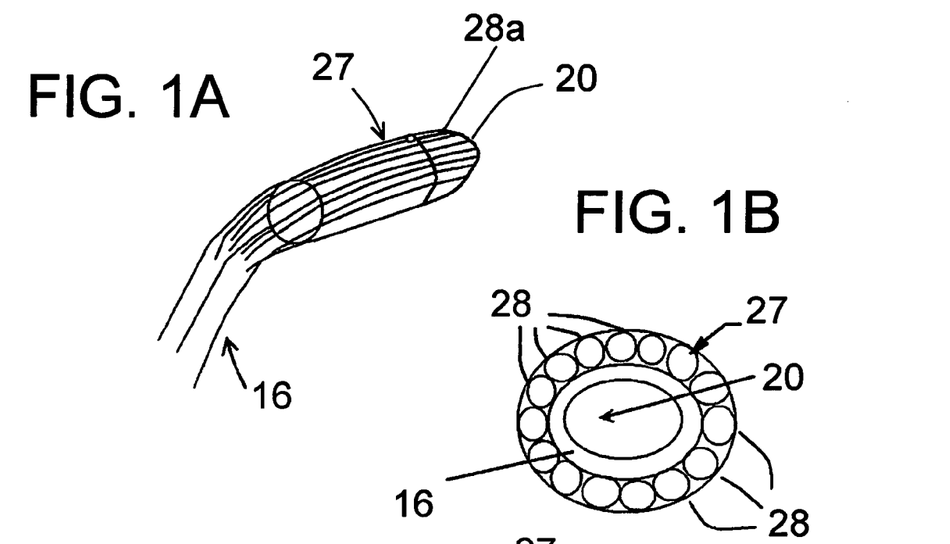
FIGS. 1A, 1B and 1C schematically show a shielding device at the end of an applicator, for selectively controlling direction of radiation from a source.
Figure 1C:
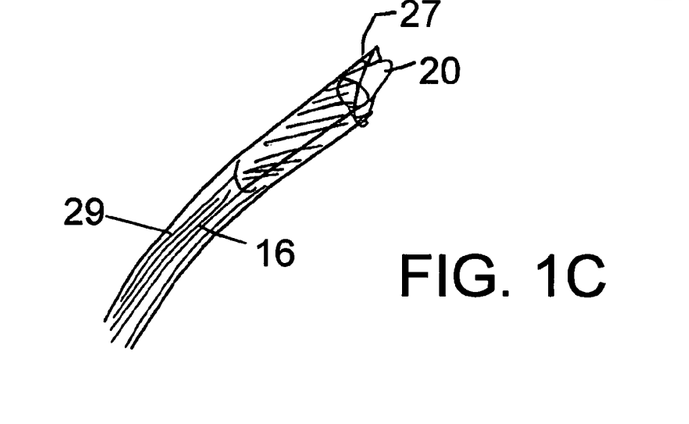

FIGS. 1A, 1B and 1C are schematic drawings showing an example of a segmented shield type beam directionality device. The source 20 is at the end of a catheter 16, which has at its tip a shielding device 27 that consists of an annular array of finger-like shield segments 28. These finger-like segments 28, exposed at their ends 28a, are each slidable within a channel of the catheter or applicator 16, as generally indicated at 29 in FIG. 1C. The annular array of shield segments 28 can be manipulated from the proximal end of the probe or catheter, i.e. from the control end of the probe outside the patient. Control can be hydraulic, with liquid such as saline solution controlling the position of the finger-like segment in each channel, or the individual segments 28 can themselves extend back to the control area. In either event, the segments can be manipulated by extension or retraction to form the desired size and orientation of radiation "window", as shown in FIGS. 1A and 1C. The direction of radiation can be selected and can be rotated, without requiring rotation of the probe itself. Note that all shield segments can be retracted, or all can be extended, for controlling radial versus strictly distally-directed radiation.

Although the use of such a treatment plan can be helpful to the radiologist, the feedback control makes comparisons to the prescription dose, not to the treatment plan, which is only a plan for emitting radiation at calculated levels at specific dwell times and for manipulation of the catheter in an attempt to deliver the correct dose profile. In one preferred embodiment of the invention the conventional treatment plan can be eliminated altogether, with only a skeletal framework to be used for mechanical movements of the source during the therapy. For example, a basic source manipulation routine might simply comprise a series of pullback steps, preferably with nominal dwell times. The dosimeters sensing the cumulative dose feed back information to the processor 14 which adjusts based on this information, thus entirely controlling dose delivery in real time. This is discussed further below.

Figures 2, 3:
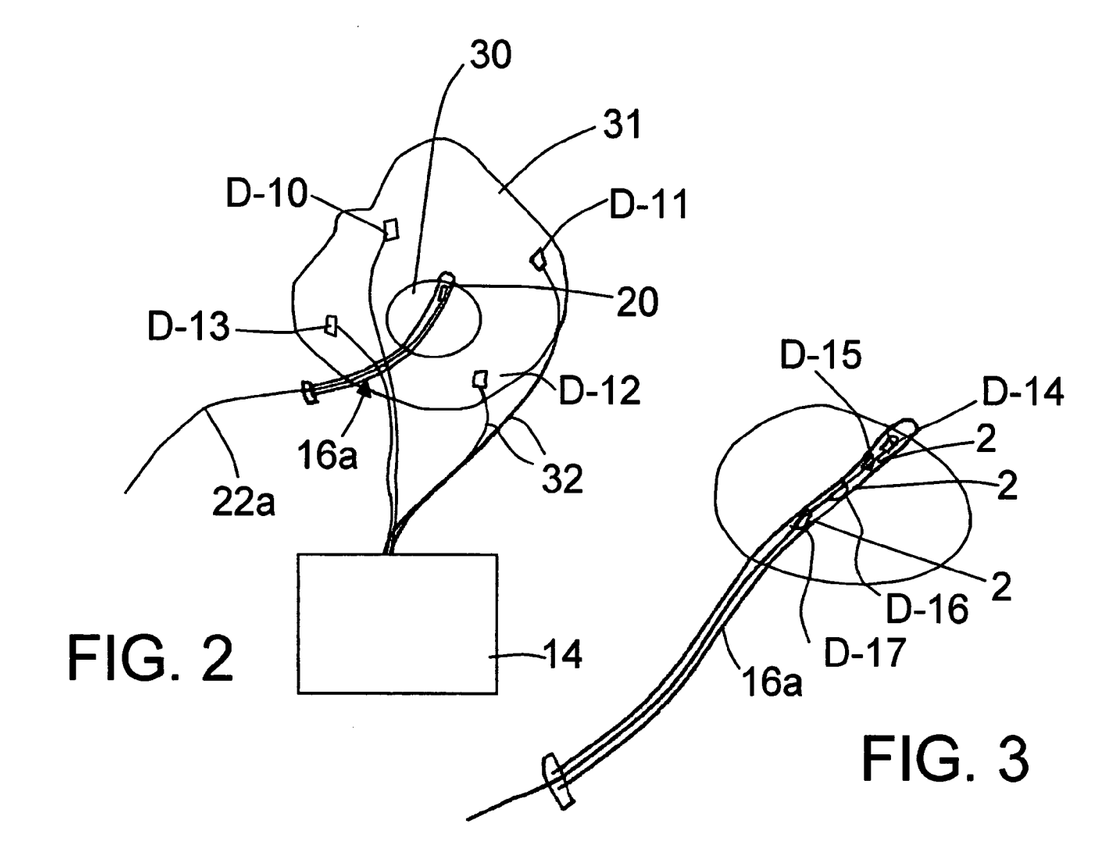
FIG. 2 is a schematic view showing further locations of sensors and other components of the system of the invention.
FIG. 3 is a view showing an applicator that can be used with the system of the invention.

FIG. 2 shows a controller 14 and a series of dosimeters, as they can be placed in or on a mass of patient tissue 31, with an applicator shown at 16a. The dosimeters D-10 through D-13 are shown surrounding a cavity 30 which can be a resection cavity or another cavity of the body, with the applicator 16a (which may be curved as shown) extending into the cavity 30. The applicator 16a is of a type without a balloon. The placement of the dosimeters D-10 through D-13 is such as to provide feedback information as to dose received in the target tissue itself, as a direct measure as to whether the correct amount of radiation is received, and preferably at non-target critical locations that cannot be over-radiated. Again, although wires 32 are shown connecting the dosimeters to the controller 14, the communication can be wireless if desired.

In FIGS. 3 through 6 additional illustrations are provided for dosimeter placement. It should be understood that the different placements shown in these figures, including FIG. 2, can be combined in any way desired. In FIG. 3 the applicator 16a has dosimeters on the applicator itself, shown at D-14 through D-17. This sensor placement is also shown in copending application Ser. No. 11/324,772, incorporated herein by reference. With the dosimeters on the applicator, feedback is provided as to the strength of radiation leaving the applicator and this can be extrapolated to compute dose at the target tissue. With dosimeters only on the non-expandable applicator, this does not provide as much feedback information as is provided, for example, in the system shown in FIG. 1.

Figures 4, 5:
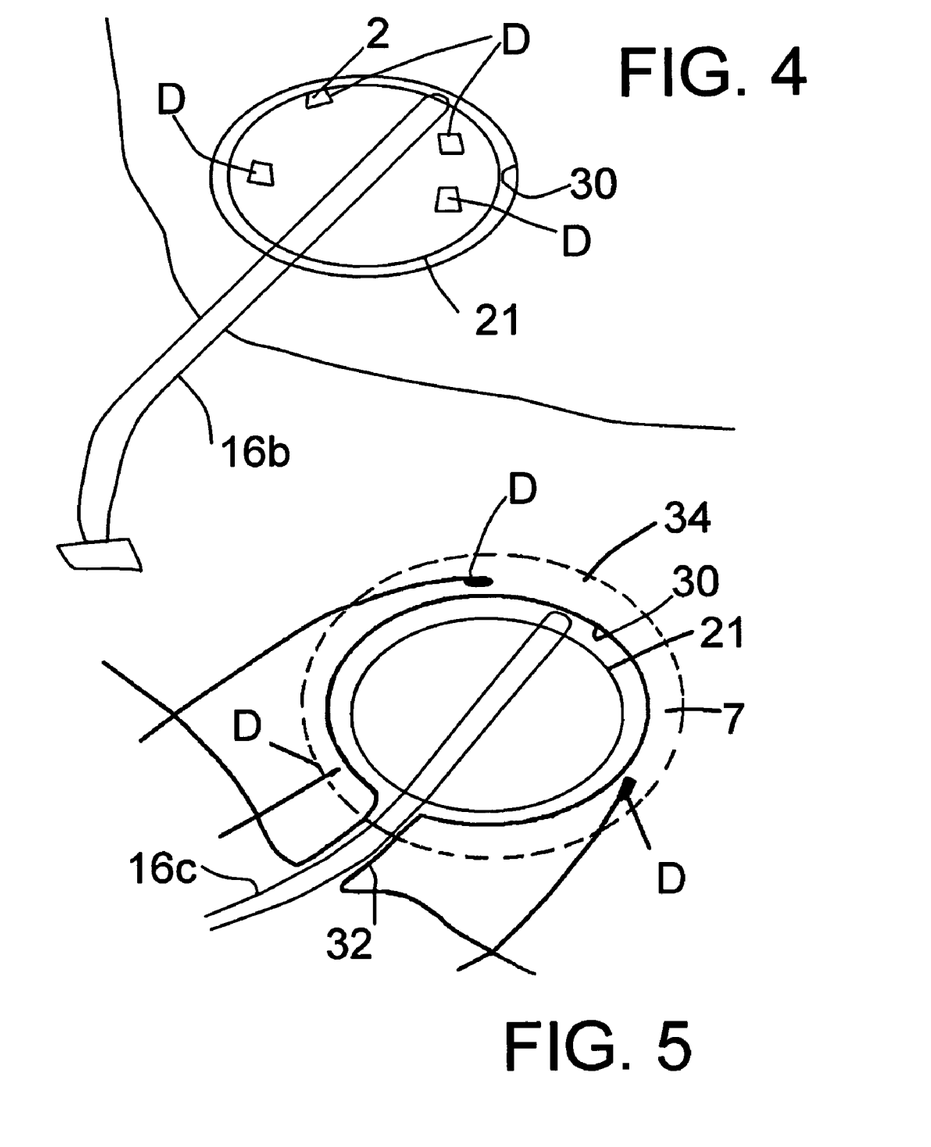
FIG. 4 is a view showing another form of applicator.
FIG. 5 is another view showing location of sensors in accordance with the system of the invention.

FIG. 4 shows a preferred location of sensors or dosimeters, indicated generally with the reference D, located on the surface of a balloon 21 of an applicator 16b. The balloon 21 is shown expanded in a cavity 30 of a patient, such as a resection cavity. Preferably the balloon is expanded into contact with the target tissue at the boundary of the cavity 30. This is a preferred position for sensors because it puts them directly at sites where the tissue is located, so that the dose sensed is that received at the boundary tissue, and the dose to a prescribed depth in the tissue can easily be calculated.

In FIG. 5 dosimeters D are shown positioned interstitially in a patient's tissue, in positions surrounding the resection cavity 30 or other cavity of the patient. The applicator 16c is shown inserted through a surgical opening 32 to extend into and through the cavity 30. The balloon 21 of the applicator is not shown as having sensors in this view, but it can have them. The interstitially positioned dosimeters D are inserted via needles and can be connected to the processor/controller (FIG. 1) by wires or through wireless communication. The dotted boundary line 34 in FIG. 5 indicates the boundary of a volume to be irradiated which may be, for example, about 0.5 cm, 1.0 cm or 2.0 cm outwardly from the cavity boundary in all directions. The interstitial positioning of the dosimeters D in this implementation of the invention gives important dose information directly in the tissue to be targeted, at known distances from the tissue boundary (which could be accurately established by x-ray, ultrasound or other exterior imaging, for example).

Figure 6:
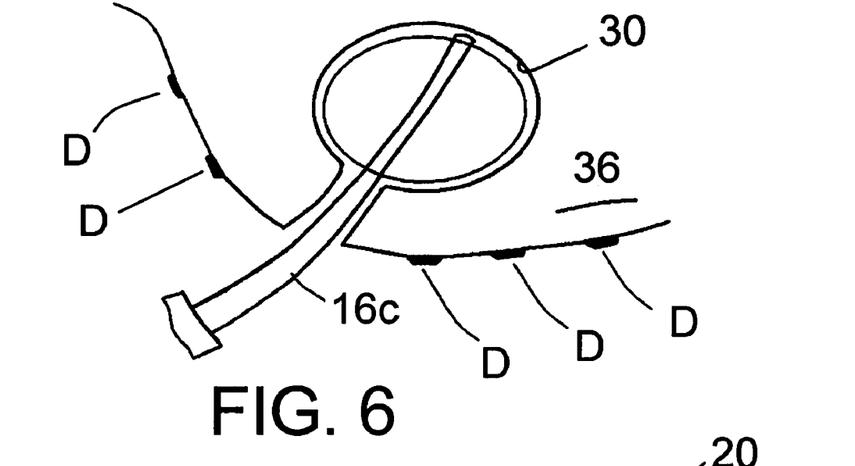
FIG. 6 is another similar view showing another placement of sensors.

FIG. 6, another sectional profile view schematically showing dosimeter placement, indicates dosimeters D placed on the skin surface. This dosimeter placement typically is in combination with other dosimeter placements, such as those in any or some of FIGS. 2, 3, 4 and 5. As shown in FIG. 6, the dosimeters D are at said skin positions close to the location of a resection cavity 30, at locations where the skin is vulnerable to radiation. The tissue 36 within which the cavity is located may be the breast, for example. By feeding back dose information from the skin at locations proximal to the cavity and the radiation source, dose information at the skin is directly fed back to the controller 14 (FIG. 1) by the dosimeters, either by wire or wireless connection, preventing excessive radiation at the skin which would cause poor cosmesis. This feedback, from each of the dosimeters D, can be used in the processor/controller 14 to reduce penetration of radiation in directions that would most affect the skin, while still assuring that the target tissue surrounding the resection cavity receives the appropriate dose (which can be supplemented by feedback information from sensors placed in other locations, such as shown in FIGS. 2-5).

Figure 7:
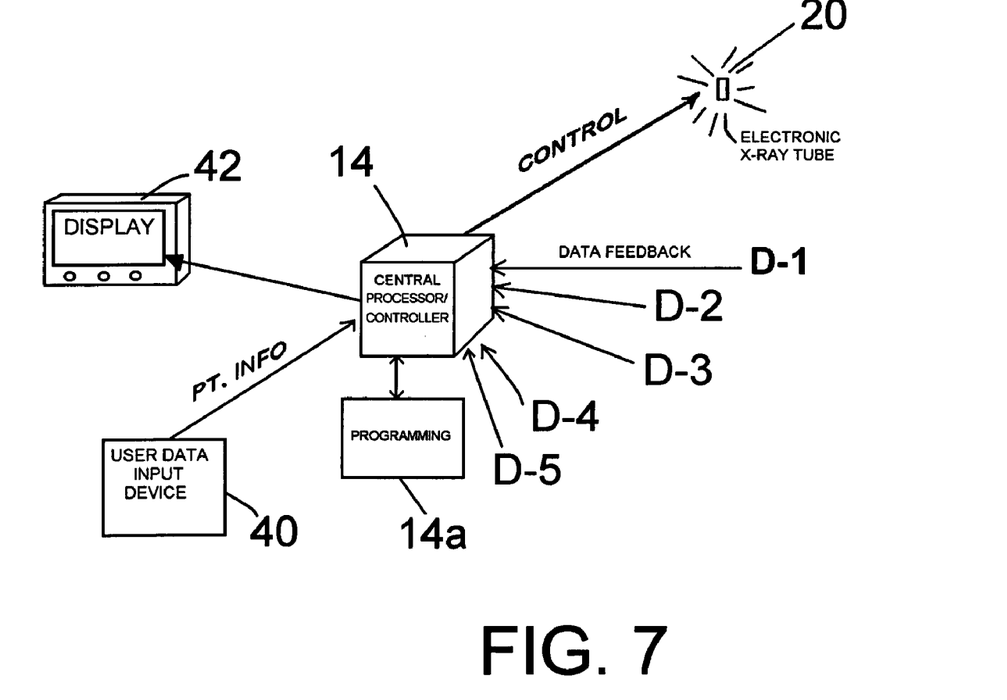
FIG. 7 is a schematic view indicating flow of information, data and control for the system of irradiation according to the invention.

FIG. 7 is a schematic system diagram for the preferred embodiment of the method and system of the invention. In this form of the invention the central processor/controller 14 does not operate from a treatment plan as such. Through the programming 14a or through a user input device 40, a basic treatment procedure comprising mechanical steps can be set up for the manipulation of the source 20 in treatment of the patient. This might include, for example, a series of ten different positional steps and a dwell time for each step, or at least a dwell time for an initial low-intensity iteration through the steps. As explained above, the x-ray source 20 on the catheter is controllable as to voltage, current and on/off status, and, in a preferred embodiment, also as to rotation (which can include speed of rotation), and as to directional radiation (rotation and directionality can be controlled by movable shielding and as shown in FIGS. 1A-3A and explained above). The system can also include a display monitor 42, which can show progress of the procedure or which can visually indicate to the radiologist steps to be taken in manually manipulating the electronic x-ray source 20 in terms of pullback position, dwell, rotation and optionally directionality and shielding.

Figure 10:
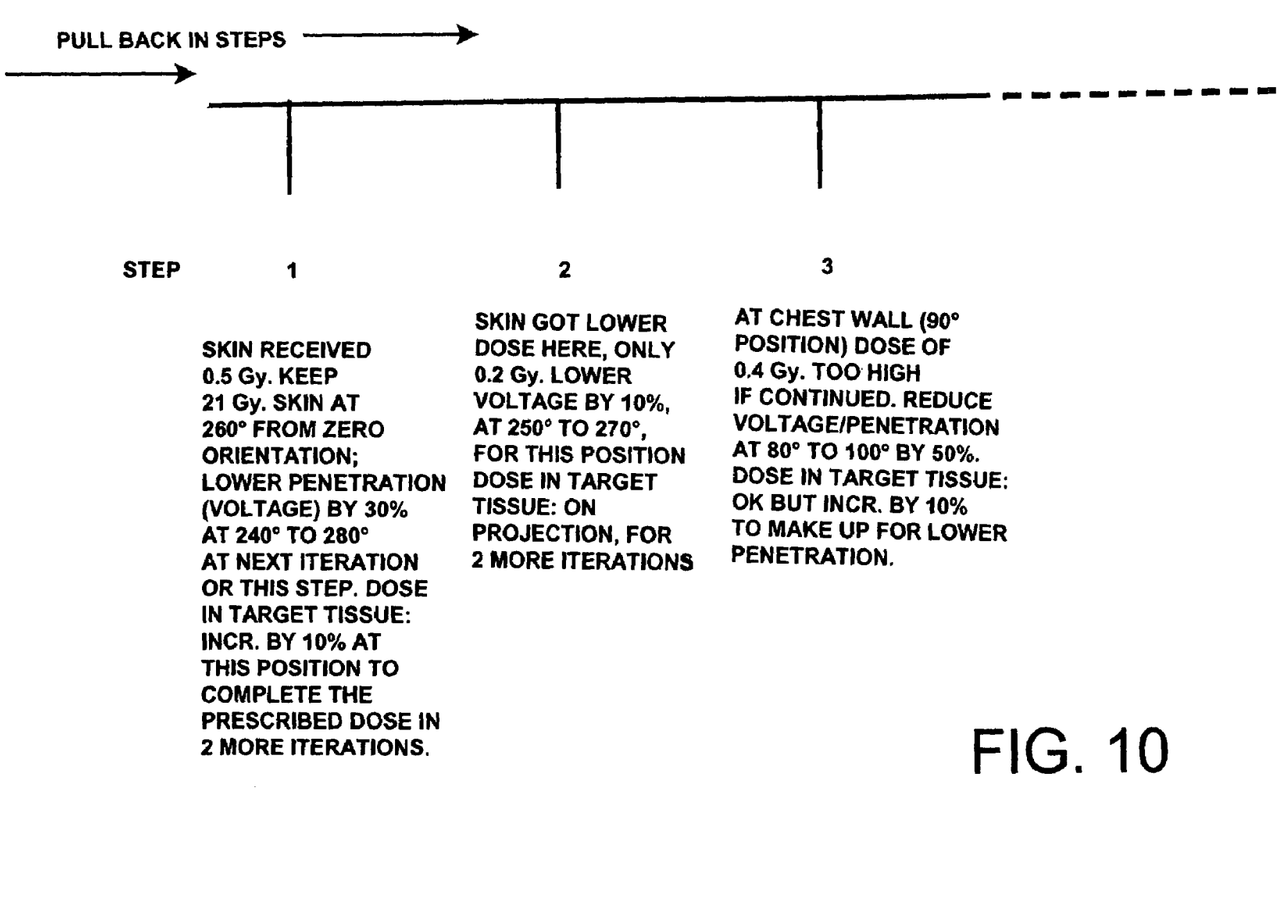
FIG. 10 is a chart schematically indicating an example of an irradiation procedure of the invention, to indicate some of the logic in the progress of the procedure, as to adjustments of the treatment plan and dose delivery based on real-time feedback.

In the procedure such as implemented by the system of FIG. 7, without a treatment plan as that term is conventionally understood, the system, under control of the processor/controller 14, initially switches on the x-ray source 20 and then goes through an initial routine at radiation levels which will be known to produce safe and under-threshold radiation at all locations. The voltage for the tube, i.e. the depth of penetration of the radiation, can be set at a high level so that all dosimeters will receive a dose that can be measured; the current or the dwell time can be limited so that the cumulative dose is relatively low in all regions of tissue. By this procedure, a first iteration could be a continuous pullback or it could be more preferably a series of about five to ten dwell positions. The dosimeters D-1, D-2, D-3, etc. feed back dose information to the controller 14. This can be from dosimeters on the applicator (such as on a balloon), interstitially positioned, on the skin, and other placements as described above. This produces a large amount of information for the controller 14, which then calculates what changes should be made assuming the procedure is reiterated at different values for one or more additional iterations. FIG. 10 shows one example of decisions made for three dwell positions. The information in FIG. 10 is only an example and is extremely simplified. It is based on results of a first iteration where readings are taken from known settings of the x-ray source 20 at a series of positions.

FIG. 10 indicates, as an example, that at position 1 the skin received 0.5 Gy, and that total dose at the skin should be kept below 1 Gy. It also shows an input (which may be a user or machine input) that the skin at this particular dwell position is at 260° from a "zero" orientation of the source 20. The controller determines that penetration must be lowered in the direction of the skin, thus the decision to lower voltage by thirty percent in a range of rotational positions, say, 240° to 280° for the next iteration at this step. Also indicated at this position in FIG. 10 is that the dose in the target tissue was insufficient for continuation at the same level of radiation, so that dose should be increased by ten percent to complete the prescribed dose in the number of further iterations prescribed, shown here as two more iterations. This increase can be by increasing the current to the tube, or by increasing dwell time at this dwell position.

At the step 2 position in FIG. 10, it is indicated that a lower dose was received at the skin, about 0.2 Gy. Thus, voltage is to be lowered by about ten percent for the next iteration, in rotational positions between 250° and 270°. The drawing also shows in this example that dose in the target tissue was on projection, for completing the procedure in two more iterations. There could be an adjustment needed to compensate for lowering of the voltage. The system can calculate that dose should be increased, at least in the region from 250° to 270°, in order to keep the dose on target. Similarly, the system might compute that voltage should be increased in some angular positions surrounding the angular region where voltage was decreased, depending on the position of the tube and the orientation of the axis about which the tube and catheter rotate, as compared to the position in angular relationship of the skin or other critical tissue to the radiation source.

FIG. 10 also shows adjustments at step position 3. It is indicated that the chest wall is at the 90° position relative to the zero rotational position of the tube. A dose of 0.4 Gy was received at the chest wall, which is too high if continued. It is calculated that voltage should be reduced in the region 800 to 100° by fifty percent. It is also noted that dose in the target tissue was on target, but dose is to be increased by ten percent to compensate for lower penetration in the next few iterations. Such increase in dose can be limited to a certain angular region if warranted.

FIG. 10 only shows three dwell positions; normally there will be more. By the procedure outlined above, the need for a conventional treatment plan is avoided and the feedback control system of the invention directly controls radiation as it is accumulated, to arrive very close to target dose prescription at all regions of the tissue, while avoiding damage to vital organs and other tissue that cannot be over-radiated. The complex calculation of a detailed treatment plan to achieve the prescribed dose is not needed, and a much more accurate procedure is put in its place, determining the effect of a preliminary iteration of radiation empirically and relatively precisely. With data gained from an initial iteration of the steps, the processor/controller 14 can use and determine precise data for dose to be received from selected dwell positions and settings, and this information includes the effect on a point of tissue of radiation from a near dwell position as well as radiation from all other dwell positions in the procedure, a complicated integration if done by calculation, particularly for irregular cavity shapes. The only parameters that need be set for the preliminary iteration are the current and voltage settings to the tube, dwell time at each position and directionality and rotation, if any, all of which will be set to deliver conservative radiation to all points; and the positions of the dwell points themselves.

Further, the system of FIGS. 7 and 10, by measuring and feeding back dose information and making corrections, which can be reiterated several times on-the-fly, avoids the need for detailed mapping such is described in copending application Ser. No. 10/464,140. Such detailed three-dimensional mapping as described in the copending application to support calculation of a detailed treatment plan, especially for irregular cavity shapes.

Figure 8:
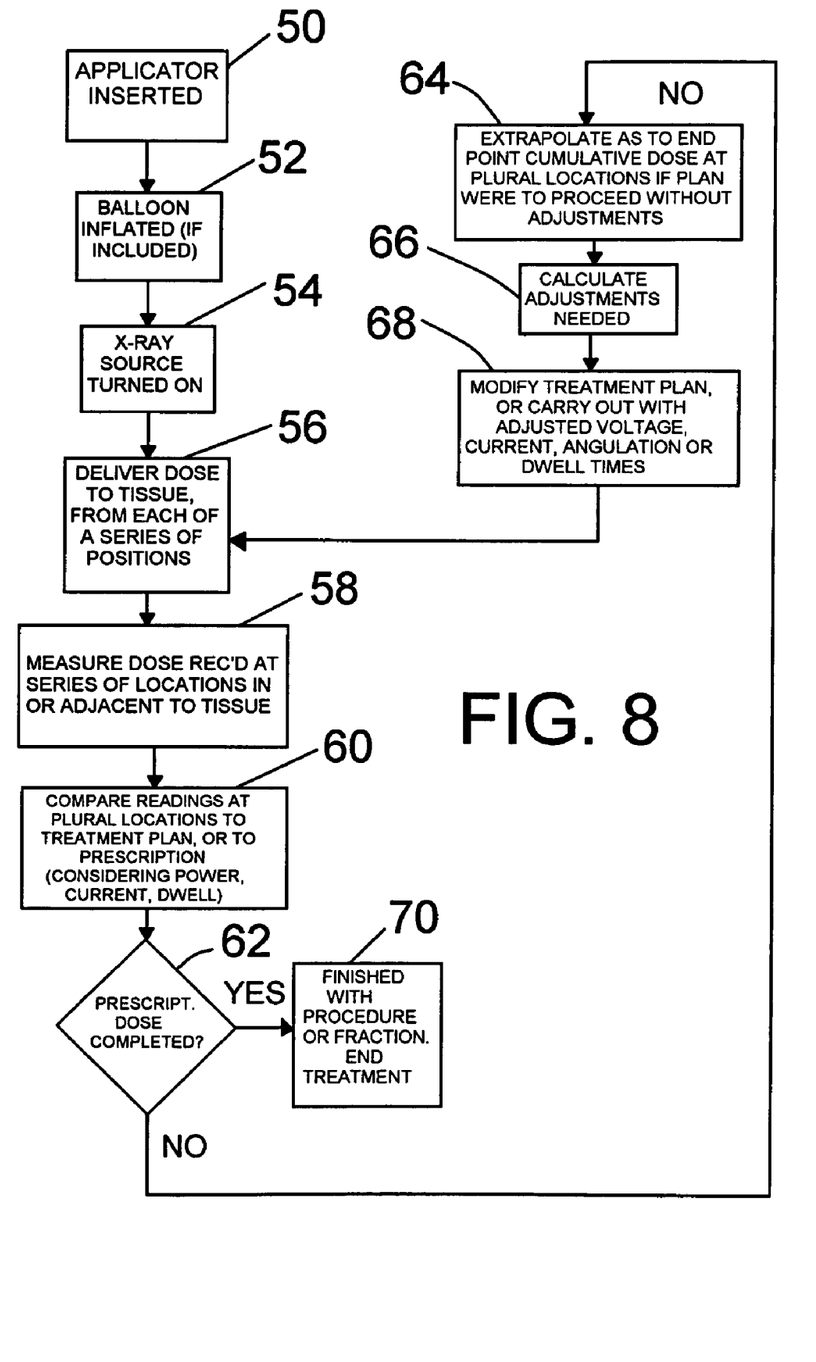
FIG. 8 is a flow chart indicating the system and the procedure of the invention.
Figure 9:
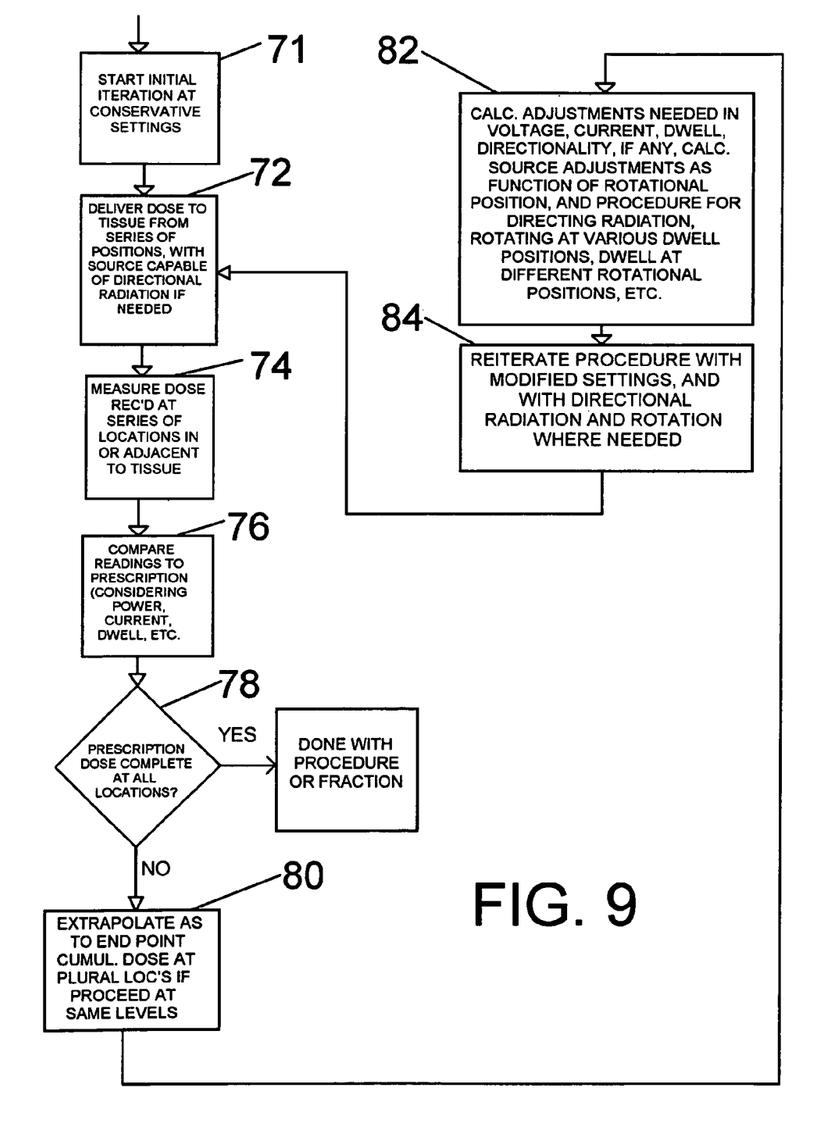
FIG. 9 is another flow chart showing similar flow of procedural steps but with some modifications and showing greater detail regarding the feedback of information and the responsive control effected based on that feedback.

FIGS. 8 and 9 are flow charts showing procedures of the invention, with FIG. 8 assuming a treatment plan in place and FIG. 9 assuming no treatment plan but with the real-time monitoring procedure just described. In FIG. 8 the applicator is inserted at block 50. The balloon, if included, is inflated, shown at 52. The x-ray source is turned on (54) and dose is delivered to the tissue, from a series of positions, in accordance with a previously calculated treatment plan, as indicated at 56. At the same time, the sensors measure dose received at a series of locations in or adjacent to the tissue, shown in the block 58, preferably as radiation is delivered from each dwell point. The dose information from each sensor is fed back to the processor/controller.

The procedure assumes more than one iteration through the dwell positions to complete an irradiation procedure, which usually is a fraction. "Iteration" does not refer to a fraction. In subsequent fractions (if any) the initial settings can be more accurate, based on data gained from the first fraction (or the system can start anew with each fraction). If a single iteration were to comprise the entire fraction, accurate and effective real-time adjustments could not be made for all treatment regions (although over-radiation at certain tissues could be prevented), because the actual effect of radiation emitted from each dwell position on tissue near each of the other dwell positions is not yet known, although treatment plan calculations could be relied upon for an approximation. Real-time monitoring and modification of treatment is an important and central feature of the invention, establishing accuracy through on-the-fly, real-time adjustments, that cannot be obtained using a treatment plan that is only projected to provide prescribed dose. Verification that the correct dose was received in all target tissue, and prevention against overdosing, are critical features that cannot be achieved by mere calculation and projection. If a detailed treatment plan is calculated and prepared, and is being carried out as closely as possible, then feedback from the sensors can be used to make adjustments that will improve accuracy in the event conditions are not as assumed in making the calculation. For example, if the tissue being penetrated attenuates the radiation to a greater degree than expected, or if the x-ray source does not perform entirely as expected, this can be determined at the first dwell position or at the first two dwell positions, for example, by measuring that the radiation at several sensor points due to this single dwell position (or two dwell positions) is different from what was expected from calculations. The system can then adjust voltage and/or current to compensate for this difference, in a way that will produce closer-to-target dose at tissue near at least the remaining dwell positions. Without further iterations the tissue at the initial dwell positions cannot be fully compensated, but still a better result can be achieved than without real-time adjustment.

Returning to FIG. 8, the system compares readings from plural sensor locations to the treatment plan or to the prescription. This is against the backdrop of the settings for power, current, dwell time and directionality that have been used, and which can be adjusted if needed (block 60). Comparison to the treatment plan is relevant to performance of the radiation source, since the plan relies on a certain radiation level being emitted in order to achieve the desired result. However, the important comparison is to the prescription dose, where the prescription dose is for the particular fraction now being administered, because this is the feedback comparison relating to the actual result achieved. In other words, a mere verification that treatment is according to the treatment plan only verifies that radiation emanating from the source was what was according to plan; it does not verify that dose received at tissue positions is in accordance with dose prescription.

The block 60 indicates the comparison just described. Following this a decision block 62 indicates a check as to whether the prescription dose has been completed. The answer will typically be NO for feedback from the first few dwell positions, at least in the first iteration, since not all tissue will have received the prescription dose at this point. However, through modifications and continued loops in the flow chart of FIG. 8, the prescription dose at all locations eventually will be essentially completed. Adjustments can be made even during the first iteration for further dwell positions if desired; the primary adjustments, though, preferably are between iterations through all dwell positions.

When the decision to the block 62 is NO, the blocks 64 and 66 indicate that the system performs appropriate calculations to figure modifications needed for the tube settings or dwell times. In the block 64 is noted that the processor extrapolates as to end point cumulative dose at plural tissue locations in the event the plan would proceed without adjustments. From this information, the system calculates adjustments needed, as shown in the block 66. The block 68 then indicates that the treatment plan is modified, or if not formally modified, it is carried out with adjusted voltage, current or dwell times for the source. The loop returns to the block 56. This indicates carrying out further dwell positions at different source and/or dwell settings. Thus, the procedure shown in FIG. 8 can be repeated for each dwell position.

When the query at the decision block 62 determines prescription dose is completed in all tissue regions (which can be met within a predetermined range), the procedure is completed relative to the treatment or particular fraction, as in the block 70.

FIG. 9 shows a portion of the loop of FIG. 8, but modified to the preferred embodiment wherein a treatment plan need not be prepared, nor is detailed tissue mapping needed. The initial blocks for start-up of the procedure, such as 50-54 in FIG. 8, still apply but are not shown in FIG. 9. The block 71 in FIG. 9 indicates start of an initial iteration at conservative settings of the source and of dwell times. One iteration will proceed through all dwell positions. The block 72 indicates delivery of radiation dose to the patient's tissue from each of the series of dwell positions, preferably using a source capable of directional radiation and with directional control, if needed. The dose received is measured at a series of locations in or adjacent to the tissue (block 74). In the block 76, the system compares the actual dose readings to the dose prescription (with interpolation/extrapolation as to tissue position as needed), considering settings of power, current and dwell that are used in this initial iteration, and considering the number of iterations that are tentatively planned. At a decision block 78 is the inquiry as to whether the prescription dose has been completed at all locations. As in FIG. 8, the answer typically will be "NO" initially. Although the inquiry preferably is carried out through all iterations, it should not be relevant for the first iteration, because settings are very conservative for this initializing iteration.

The blocks 80 and 82 show a framework for calculating adjustments needed. In the block 80 the system is shown as extrapolating end point cumulative dose at a series of locations assuming the system proceeds through the tentatively planned number of iterations at the current settings. From this the needed adjustments are calculated (82) for voltage, current, dwell and directionality, if any. For specific situations source adjustments are calculated as functions of rotational position, and a procedure for directing the radiation, rotating at various dwell positions, varying dwell for different rotational positions, etc., is calculated (note that directionality and "rotation" of radiation can be via shielding, as discussed above). See FIG. 10 for a simplified example of a portion of an adjustment routine. In one routine of a preferred embodiment the system calculates modified radiation settings such as approximately to produce, on each further iteration, an overall dose in proportion to the remainder of total dose to be delivered. This will only be a projection, and nearly always further adjustments will be needed.

The block 84 indicates reiterating the procedure, through a next iteration at all dwell points, with the modified source and dwell settings, and with directional radiation and rotation where needed. The flow then proceeds back to the block 72, and monitoring for accuracy continues.

With the procedure as in FIG. 9, and also discussed relative to FIGS. 7 and 10, the target procedure can be for several iterations, or for many iterations, e.g. five to ten iterations if desired. In general mote iterations within a fraction can enable greater accuracy, because the application of radiation is more conservative and incremental. Even if the procedure for a fraction is for a set number of iterations, such as five, one or more further iterations can be initiated by the system if the fifth iteration indicates certain tissue regions did not receive the full dose. Thus, especially with directional radiation and rotational control capability, the system can go back, skip dwell positions where not needed, and irradiate tissue in a specific and targeted manner (with depth and dose control) to complete the dose as prescribed for all regions. The processor/controller can also make decisions as to permitted overages at certain regions of tissue in order to fully irradiate tissues beyond. Since tissue most-distant from the source requires that radiation pass through tissue more proximate to the source (and the inverse square relationship and absorption provide for sharp fall-off of intensity with distance), such decisions will often be needed. Settings can be input by the physician/radiologist, via the input device 40 shown in FIG. 7. Such input parameters can include permitted percentage of overdosing in the proximate tissue, and permitted percentage of underdosing at more remote tissue, as set by specific depths, etc. Note that multiple radiation sources can be used at the balloon surface, as in copending applications Ser. Nos. 10/464,140 and 10/683,885, to greatly reduce the effects of inverse square fall-off; the content of those copending applications is incorporated herein by reference.

Although the procedures above refer to stepped pullback of the radiation source, i.e. emitting radiation from a series of dwell positions, the pullback can be continuous. Source position is always known to the processor; speed of movement can be varied and with directional control the rate of sweeping the radiation can also be varied. The radiation can be emitted continuously (or with interruptions as needed) in a rotating sweep forming a helical path at the tissue as the service is pulled back. Or, indexing can be used in either the rotation or the pullback in order to achieve the desired pattern and dose profile. With continuous movement the feedback from the sensors can be more frequent than the dwell positions in stepped pullback. Continuous pullback with frequent feedback and adjustment potentially can be more accurate than stepped pullback, for irregular shapes. For a particular cavity (or other treatment region) shape the operator or the controller should generally choose the most straightforward pullback routine that will achieve the desired dose profile in the tissue.

Although more dynamic in radiation delivery, the continuous procedure with monitoring can be operated essentially the same as outlined in FIGS. 9 and 10 with modifying adjustments made on the fly.

Movement of the patient during the procedure (or between fractions) can also be an issue, particularly in breast radiation, where imaging may be done in one part of the treatment facility and radiation delivered in another. The system of the invention not only can avoid the need for therapy, but also avoids the need to move the patient. And, with a relatively high number of multiple iterations in the procedure described above, the effects of movement can be fully compensated. If, for example, the tissue shifts in such a way that the x-ray tube is considerably closer to the skin in a subsequent iteration, the system will automatically compensate by noting the increased dose at the skin. The more the procedure within a fraction is divided into iterations, the more conservative each iteration and the more accurate the result with respect to shifts in position.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A method for treating a patient with radiation therapy which includes brachytherapy, comprising:
    a step for localizing the region to be irradiated, including determining the shape and location of the region,
    preparing a radiation treatment plan for the region, based on the determined shape and location of the region and on a radiation prescription, with a prescribed dose for each of different portions of the region,
    inserting a probe into the patient, the probe having an ionizing radiation source, to a position for delivering radiation to the region,
    delivering radiation to the region using the ionizing radiation source, pursuant to the radiation treatment plan,
    while delivering radiation, monitoring dose delivered at a plurality of points in or near the region, and
    as needed, modifying delivery of radiation based on dose as monitored, to arrive at generally a prescribed dose in tissue at all portions of the region.

2. The method of claim 1, wherein the step of monitoring dose delivered comprises using sensors on the probe.

3. The method of claim 1,.wherein the step of monitoring dose delivered comprises using sensors within a cavity located at the region to be irradiated.

4. The method of claim 1, wherein the step of monitoring dose delivered comprises using sensors carried on a balloon on the probe, the balloon being inflated into a cavity located at the region to be irradiated.

5. The method of claim 1, wherein the step of monitoring dose delivered comprises using sensors positioned interstitially in the patient near the region to be irradiated.

6. The method of claim 1, wherein the step of monitoring dose delivered comprises using sensors positioned externally on the patient.

7. The method of claim 1, wherein the radiation is delivered in fractions, and wherein the step of modifying delivery is performed within fractions and between fractions.

8. The method of claim 1, wherein the radiation is delivered in fractions, and wherein the step of modifying delivery is performed within a fraction.

9. The method of claim 1, including use of a central processor to prepare the radiation treatment plan based on a determined shape and location of the region and on the prescribed dose, to receive real-time monitoring information from the sensors, and to modify the treatment plan and the delivery of radiation in real time prior to delivery of the complete prescribed dose.

10. The method of claim 1, wherein the region to be irradiated is adjacent to and surrounding an incision cavity.

11. The method of claim 9, wherein the ionizing radiation source comprises a controllable electronic radiation source.

12. The method of claim 11, wherein the controllable ionizing radiation source can be varied as to voltage and as to current for varying radiation penetration depth and for varying dose delivered, and the delivering step including delivering the radiation by varying voltage and/or current to produce the prescribed dose in accordance with the treatment plan for the different portions of the region, and wherein the modifying delivery step includes modifying voltage or current in the electronic source as needed substantially to achieve and substantially not to exceed the prescribed dose to each of the different portions of the region.

13. The method of claim 11, including communicating between the central processor and the electronic radiation source, with Dicom RT protocol.

14. The method of claim 11, including communicating between the central processor and the electronic radiation source with wireless communication.

15. The method of claim 14, wherein the wireless communication is UWB.

16. The method of claim 9, further including storing in the central processor patient information including patient identity, radiation fraction schedule and procedure outcome.

17. The method of claim 1, wherein the ionizing radiation source comprises a controllable electronic radiation source.

18. The method of claim 1, wherein the step of determining the shape and location of the region includes mapping the three dimensional shape and location of the region using at least one sensor and at least one radiation source, and wherein at least one of the sensors used in mapping is also used in monitoring dose delivered, as the radiation is delivered in accordance with the treatment plan.

19. A method for achieving a targeted dose profile in brachytherapy radiation treatment on a patient, comprising:
inserting an applicator into the patient, at a site desired for administering brachytherapy, the applicator having at least one onboard dosimeter sensor, each sensor being at a position to be directly adjacent to tissue to be irradiated,
using a treatment plan calculated for the patient, commencing irradiation using an electronic radiation source in the applicator and during irradiation, sensing dose received at least at one dosimeter sensor on the applicator, adjacent to the tissue,
feeding back to a controller data on dose received at each of the dosimeters, at least at repeated intervals during the procedure, and
automatically adjusting in real time, based on the dose information fed back to the controller, the radiation emitted by the radiation source in the applicator, so as to adjust actual received dose at multiple locations in the tissue as the radiation procedure continues, in a way that repeatedly readjusts the treatment plan and the radiation being emitted so as to achieve a projected total dose profile which meets the targeted dose profile.

20. The method of claim 19, further including sensing dose received at additional dosimeter sensors not on the applicator and in or near the tissue to be irradiated.

21. A method for achieving a targeted dose profile in brachytherapy radiation treatment on a patient, comprising:
inserting a probe into the patient, the probe having an electronic radiation source, to a position for delivering radiation to the tissue to be irradiated, and placing at least one dosimeter in or adjacent to the tissue to be irradiated,
commencing irradiation using the electronic radiation source and during irradiation, sensing dose received at the at least one dosimeter,
feeding back to a controller data on dose received at each of the dosimeters, at least at intervals during the procedure, and extrapolating as needed with the controller to determine dose at additional tissue positions lacking dosimeters, and
automatically adjusting in real time, based on dose information fed back to the controller, the radiation emitted by the electronic radiation source, so as to adjust actual received dose at multiple locations in the tissue as the radiation procedure continues, in a way that repeatedly readjusts the radiation being emitted so as to achieve a projected total dose profile which meets the targeted dose profile.

22. The method of claim 21, wherein the method is carried out without a treatment plan.

23. The method of claim 22, including carrying out the irradiation of the tissue in multiple iterations each being insufficient to produce the prescription dose to the tissue, a first iteration being performed at low and conservative radiation levels known to be insufficient to irradiate any area of the tissue to the full prescription dose, and including collecting dose information from the first iteration in the controller and calculating from the dosimeter-based dose information a radiation level and pattern, projected cumulatively to produce the prescription dose in all regions of the tissue to be irradiated over one or more further iterations.

24. The method of claim 22, including carrying out the irradiation of the tissue in multiple iterations each being insufficient to produce the prescription dose to the tissue, a first iteration being performed at low and conservative radiation levels known to be insufficient to irradiate any area of the tissue to the full prescription dose, and including collecting dose information from the first iteration in the controller and calculating from the dosimeter-based dose information radiation levels and a pattern projected to irradiate the tissue in proportion to the prescription dose profile, and continuing with further iterations performed at conservative radiation levels and with settings to achieve dose generally in proportion to the prescription dose profile, and repeating iterations to treat tissue regions as needed until prescription dose is substantially achieved for all regions in a final iteration.

25. The method of claim 22, wherein the electronic radiation source is a miniature x-ray source capable of angularly-controlled directionality, and the method steps including, at least in a final iteration, adjustment of radiation levels at different angular directions at least at some of the series of dwell points in a pullback routine so as to deliver radiation only in directions needed at each dwell point to thereby complete radiation dose in a number of regions of tissue very close to prescription levels.

26. The method of claim 25, including using the angularly-controlled directionality to target only portions of a full circumference of tissue with radiation, at least at some dwell positions.

27. The method of claim 22, with at least three iterations, the first being at low levels, and each successive iteration including adjustment of voltage and/or current as needed, with each iteration approaching closer to full prescription dose at all regions, with prescription dose being reached for some regions only in a final iteration.

28. The method of claim 25, wherein the angularly-controlled directionality of the source is provided using shielding of the source and rotation of the source as the method proceeds.

29. The method of claim 25, wherein the angularly-controlled directionality of the radiation source is achieved without rotation of the source, using adjustable shielding in multiple movable segments positioned around the source.

30. A method for treating a patient with radiation therapy which includes brachytherapy without use of a treatment plan, comprising:

inputting to a controller a prescription dose for tissue to be irradiated, placing on or in the patient a plurality of dosimeter sensors, each in or near the tissue to be irradiated, each being in communication with the controller to send sensed dose data to the controller, inserting into the patient a controllable electronic radiation source, under the control of the controller, and initiating with the controller a source manipulating routine to move the source so as to emit radiation from plural locations within the patient, and monitoring radiation received at the dosimeter sensors and controlling radiation delivered by the source to different tissue locations based on dose data fed back from the dosimeter sensors, and continuing to move the source and emit radiation as selected by the controller at different locations in a plurality of iterations, until substantially the prescribed dose has been received at all tissue locations.

31. The method of claim 21, wherein the electronic radiation source is a miniature xray source capable of angularly-controlled directionality, and wherein the step of automatically adjusting the radiation includes adjusting radiation levels at different angular directions during the radiation treatment.

32. The method of claim 21, wherein the electronic radiation source is a miniature xray source capable of angularly-controlled directionality, and the method steps including adjustment of radiation levels at different angular directions at least at some of a series of dwell points in a pullback routine so as to deliver radiation in different directions only as needed at each dwell point to thereby complete radiation dose in a number of regions of tissue very close to prescription levels.

* * * * *